United States Patent [19]

Norman

[11] Patent Number: 5,508,204

[45] Date of Patent: Apr. 16, 1996

[54] MULTIPLE SAMPLE SEQUENTIAL CHEMICAL ANALYSIS

[75] Inventor: Eric J. Norman, Cincinnati, Ohio

[73] Assignee: Norman Clinical Laboratories, Inc., Cincinnati, Ohio

[21] Appl. No.: 371,952

[22] Filed: Jan. 12, 1995

[51] Int. Cl.$^6$ ..................................................... G01N 30/02
[52] U.S. Cl. ............................ 436/161; 73/23.35; 95/87; 96/103; 210/198.2; 210/656; 422/70; 422/89; 436/128; 436/129; 436/173
[58] Field of Search ..................................... 436/127–129, 436/161, 173, 145; 422/70, 89; 73/23.35, 23.25, 23.26; 210/635, 656, 198.2; 95/82, 87, 89; 96/101, 102, 103

[56] References Cited

U.S. PATENT DOCUMENTS

| | | | |
|---|---|---|---|
| 3,248,929 | 5/1966 | Webb | 73/23.35 |
| 4,096,908 | 6/1978 | Lamy | 165/64 |
| 4,805,441 | 2/1989 | Sides et al. | 73/23.1 |
| 4,948,389 | 8/1990 | Klein et al. | 95/18 |
| 5,135,549 | 8/1992 | Phillips et al. | 55/67 |
| 5,141,532 | 8/1992 | Sacks et al. | 55/67 |
| 5,268,302 | 12/1993 | Rounbehler et al. | 436/96 |
| 5,300,758 | 4/1994 | Rounbehler et al. | 219/497 |

OTHER PUBLICATIONS

Phillips et al., J. Chromatogr. Sci. vol. 24, pp. 396–399 (Sep. 1986).
Barber–Coleman Co., Whelco Instrument Division, "Simplified Block Diagram of the Barber–Colman Gas–Liquid Chromatographic Ionization Detection System, Model 10." *Whelco Instruction Manual*, pp. 7, 9.
Finnigan Corporation, "Finnigan MAT: Magnum™ GC/MS System" pp. 1–12 (1994).

Primary Examiner—James C. Housel
Assistant Examiner—Jan M. Ludlow
Attorney, Agent, or Firm—Christensen, O'Connor, Johnson and Kindness

[57] ABSTRACT

A method for analyzing multiple analyte specimens using an analytical column containing a selective adsorbent media. A carrier fluid flows through the column. The method involves introducing a first analyte specimen into the analytical column at an initial temperature. The analytical column is then heated to an intermediate temperature to cause the first analyte specimen to partially travel into the column. The analytical column is then cooled back to the initial temperature, followed by introduction of a second analyte specimen into the analytical column. The analytical column is then heated to a final temperature greater than the intermediate temperature, during which heating analytes from the first and second analyte specimen concurrently and discretely travels through, and sequentially elutes from, the analytical column. The method results in discrete bands of analyte being loaded at spaced intervals within the column, and can be used to load a multiplicity of samples for concurrent analysis. This results in sequential elution of the discrete analyte bands at the end of the analysis, providing for a substantial reduction in time as compared to running multiple samples separately. The method is well suited for the analysis of methylmalonic acid content in multiple urine specimens.

15 Claims, 7 Drawing Sheets

MULTIPLE SAMPLE SEQUENTIAL CHEMICAL ANALYSIS

FIELD OF THE INVENTION

The present invention relates to methods for analyzing multiple analyte samples, and more particularly to methods of analyzing multiple urine specimens using gas chromatography.

BACKGROUND OF THE INVENTION

It is often necessary in treating patients to analyze urine specimens to measure the presence and content of various analytes as an indication of the patient's condition, metabolism, and organ function. By way of example, there is a frequent need to test urine specimens from patients as a means of identifying vitamin $B_{12}$ deficiency. Up to seven percent of individuals over the age of 65 may have a deficiency in vitamin $B_{12}$. If this deficiency is not identified and treated, it can lead to dementia and/or nerve paralysis. A deficiency in vitamin $B_{12}$ can be identified by a high urinary methylmalonic acid (MMA) level. If a high urinary MMA level is detected early on, the patient can be treated with vitamin $B_{12}$ injections to reduce or eliminate the risks of the condition. Because of the significant pool of individuals who are at risk, there is a need to rapidly test a large number of specimens.

Current methods of urinalysis involve preparation of an individual specimen, followed by introduction of a sample from the prepared specimen into a gas chromatography column. The specimen is introduced at an initial low temperature, after which the temperature of the column is raised in accordance with a predetermined instrument program. The specimen is volatilized and is carried through the column with a gaseous carrier fluid. The column is packed or internally coated with a selective adsorbent media. Individual chemicals in the analyte composition are differently soluble in the media within the column, and are able to pass through the column at different temperatures. The result is that as the temperature is raised, bands of individual chemical components from an analyte specimen are separated, traveling through the column at different rates.

The temperature of the column is eventually raised to a temperature that is sufficient to cause essentially all volatile components to pass through and elute from the column. The eluted compounds then flow into an ion trap detector, conventionally referred to as a mass spectrometer. The output from the gas chromatograph can provide an indication of the qualitative identity of each component of the composition, by comparing the elution times of the components to the elution times of known standards, as well as a quantitative indication providing a measure of concentration. However, the mass spectrometer provides a much more definitive qualitative identification of the chemicals, as well as a quantitative measurement.

This conventional method thus involves a complete sequence of sample injection, ramp heating to an elution temperature, followed by a clean-out period where the column is increased above the elution temperature, followed by cooling to the initial temperature, for each separate specimen to be analyzed. For urinalysis to determine MMA levels, this involves a 20–25-minute minimum cycle for each specimen, which ties up the analytical instrumentation and increases the cost of analysis.

SUMMARY OF THE INVENTION

The present invention provides a method for analyzing multiple analyte specimens using an analytical column containing a selective adsorbent medium. A carrier fluid flows through the column. The method involves introducing a first analyte specimen into the analytical column at an initial temperature. The analytical column is then heated to an intermediate temperature, to cause the first analyte specimen to partially travel into the column. The analytical column is then returned to the initial temperature, followed by introduction of a second analyte specimen into the analytical column. The column is then heated to a final temperature, causing analyte from the first analyte specimen and analyte from the second analyte specimen to concurrently and discretely travel through, and sequentially elute from, the analytical column.

The method can be used to sequentially load two or more analyte specimens at discrete spaced intervals prior to ramping the column temperature up to the ultimate elution temperature. The various specimens then travel concurrently through the column. Any particular chemical common to each specimen is maintained in discrete bands corresponding to the originating specimens within the column. Concurrent analysis without loss of sample integrity is therefore provided.

The present invention thus provides a method for rapid analysis of multiple specimens, and is well suited for methylmalonic acid urinalysis using gas chromatography and mass spectrometry. The cost of analysis per specimen can be reduced due to the greater throughput for a given instrument.

The method is also well suited for analysis of other chemicals using a combination of gas chromatography and mass spectrometry. In addition, other separation methods such as gas chromatography alone, supercritical fluid chromatography, or high pressure liquid chromatography could be used. Furthermore, these instruments can be coupled with detectors including mass spectrometers, mass spectrometer-mass spectrometers, or infrared spectrometers. Introduction of multiple specimens onto a separation column can also be accomplished by changing other parameters than temperature. The inventive concept of multiple specimen sequential analysis during a single chromatographic run would remain the same.

The present invention also provides an automated system including a gas chromatogram coupled to a mass spectrometer. Multiple analyte specimens are introduced to the gas chromatograph in sequential order from an autosampler controlled by a data system. The data system also controls the temperature cycling of the gas chromatograph to provide for sequential loading of the specimens within the column and the mass spectrometer for setting parameters and recording data.

BRIEF DESCRIPTION OF THE DRAWINGS

The foregoing aspects and many of the attendant advantages of this invention will become better understood by reference to the following detailed description, when taken in conjunction with the accompanying drawings, in which.

DETAILED DESCRIPTION OF THE PREFERRED EMBODIMENT

The present invention provides for a method of concurrent analysis of multiple analyte specimens. Each specimen is introduced at an initial temperature to an analytical column. The analytical column is then heated to an intermediate temperature, which causes the first analyte specimen to enter into the column, followed by returning the analytical column to the initial temperature. The next analyte specimen is then introduced to the column, and the analytical column is again heated to the intermediate temperature. This causes the first analyte specimen to travel a short distance into the column, while at the same time causing the second analyte specimen to enter the column, so that they are spaced apart. Heating of the column is either then continued to reach the final temperature, or alternately the column is again cooled for introduction of a third analyte specimen.

This sequence of introduction at an initial temperature, heating to an intermediate temperature, and cooling to the initial temperature is repeated until the desired multiplicity of analyte specimens have been loaded into the column, with each analyte specimen spaced in succession along an initial portion of the column. After loading of the last analyte specimen, the temperature is ramped to the final temperature, which is greater than the intermediate temperature. Any given component contained in the analyte specimens will elute at the same rate. Thus each given analyte component travels through the column in discrete spaced bands, with each band corresponding to the analyte specimen from which that quantity of the component originated. The analyte bands travel concurrently and discretely through the column, and sequentially elute from the column.

Before describing the method of the present invention in greater detail, a conventional method of analysis using an analytical column, in particular, urinalysis for methylmalonic acid (MMA) by gas chromatography and mass spectrometry, shall be described, in order to better understand the invention described thereafter.

a. Prior Art Analysis of a Single Urine Specimen

Figure 1:
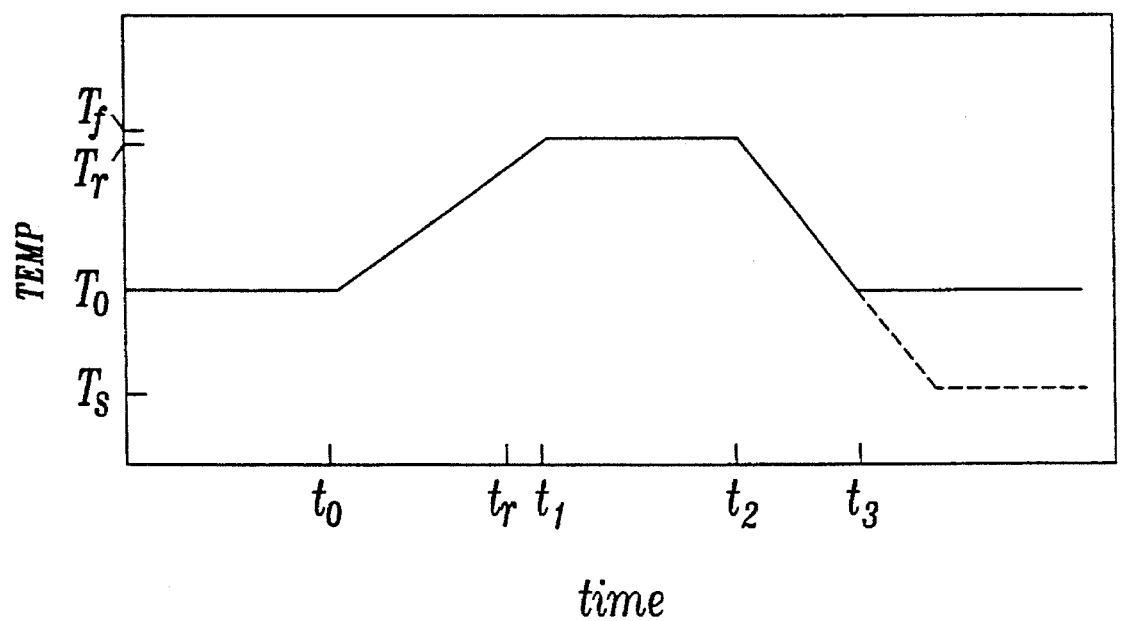
FIG. 1 provides a chart indicating a typical time/temperature operating sequence for analysis of an analyte specimen using a gas chromatograph operated in a manner typical of the prior art.

A time/temperature sequence for operation of a gas chromatograph for conventional analysis of a single urine specimen is shown in FIG. 1. The gas chromatograph is maintained at an initial temperature designated as $T_0$. At the onset of analysis, designated as time $t_0$, the sample is introduced to the inlet of the gas chromatograph column. The temperature of the gas chromatograph is then elevated or ramped at a constant rate to a temperature $T_r$, reached at time $t_r$ at which all analytes have completed elution from the column. The column is further heated to a final temperature $T_f$, slightly elevated above $T_r$, at time $t_1$, and is held at this temperature to clean out the column. At the end of this final period, designated as time $t_2$, the chromatograph is cooled back down to the initial temperature $T_0$ for subsequent analysis, which cooling down is completed at a time $t_3$. Alternately, the gas chromatogram can be cooled further down to a stand-by temperature designated as $T_s$, if no further analysis is to happen immediately.

Figure 2:
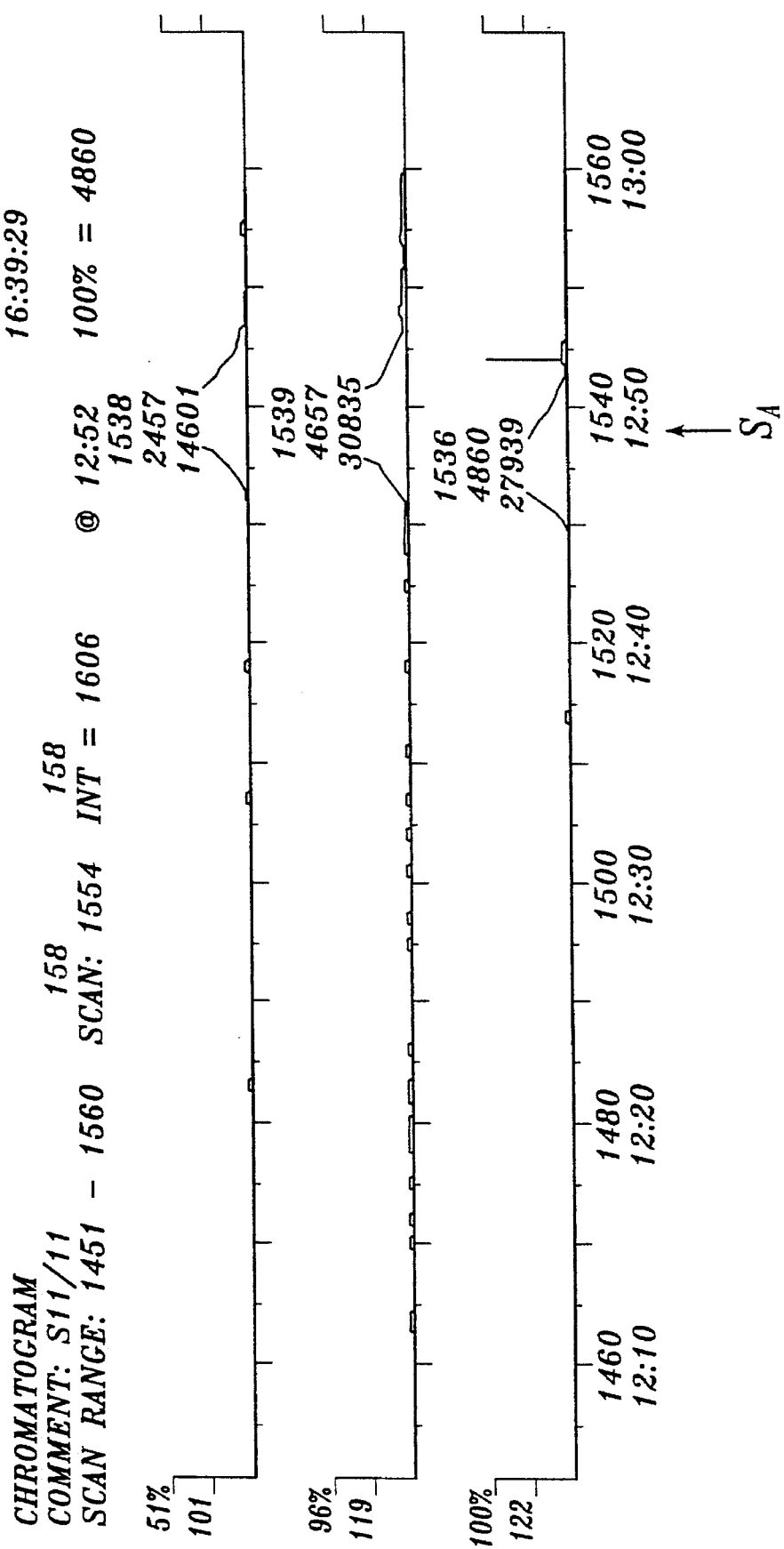
FIG. 2 provides a mass spectrometry chromatogram generated using the prior art method of FIG. 1 for the determination of methylmalonic acid (MMA) content of a single urine specimen.

FIG. 2 provides an ion trap detector output, or mass spectrometer chromatogram, produced by analyzing for MMA content in a single urine specimen using a gas chromatogram operated in accordance with the sequence of FIG. 1 coupled to a mass spectrometer. This conventional single specimen analysis method involves first preparing a urine sample by determining the level of creatinine as an indication of the overall concentration of urine. To a volume of the urine equivalent to 0.05 mg of creatinine, 500 ng of deuterated MMA is added as an internal standard. This solution is then evaporated to dryness at 80° C. and to this 200 μl of 1.5 normal hydrogen chloride in cyclohexanol is then added and allowed to react at 115° C. for fifteen minutes. This results in esterification of both the endogenous MMA as well as the deuterated MMA standard. The reaction results in methylmalonic acid dicyclohexyl esters (MMA ester) as well as deuterated MMA ester. This reaction mixture is then evaporated to near dryness, and is next redissolved in butanol to yield the prepared specimen.

This prepared specimen is then introduced to a gas chromatograph column. For the chromatogram of FIG. 2, as well as the chromatograms of FIGS. 4–6 to be described subsequently, a Varian 3300 gas chromatogram manufactured by Varian Associates, Sugarland, Tex., was utilized. The gas chromatograph was outfitted with a 30 meter DB5™ fused silica column having a 0.25 μm film thickness stationary phase of 5% phenyl dimethyl poly siloxane cross-linked and bonded to the silica surface and 0.5 mm inner diameter, available from J&W Scientific Company, Folsom, Calif. The elute from this column was received by a coupled Finnigan MAT 800 ion trap detector (i.e., mass spectrometer), available from Finnigan MAT Corporation, San Jose, Calif.

For the chromatogram result provided in FIG. 2, the prepared urine specimen was injected on the gas chromatograph at 140° C., followed by a 0.5 minute delay before increasing the temperature of the column at a rate of 10° C. per minute to a final temperature of 270° C. The analyte eluted from the gas chromatograph at 263° C. The temperature was held at 270° C. for ten minutes. The elute from the gas chromatograph was received by the mass spectrometer, the output of which is shown in FIG. 2. The MMA ester from the specimen, indicated as "$S_A$", is recorded as peaks 101 and 119, while peak 122 is the deuterated MMA ester standard. After elution of the MMA esters from specimen $S_A$, the chromatograph was cooled back to the initial temperature of 140° C.

b. Method of the Present Invention

Figure 3:
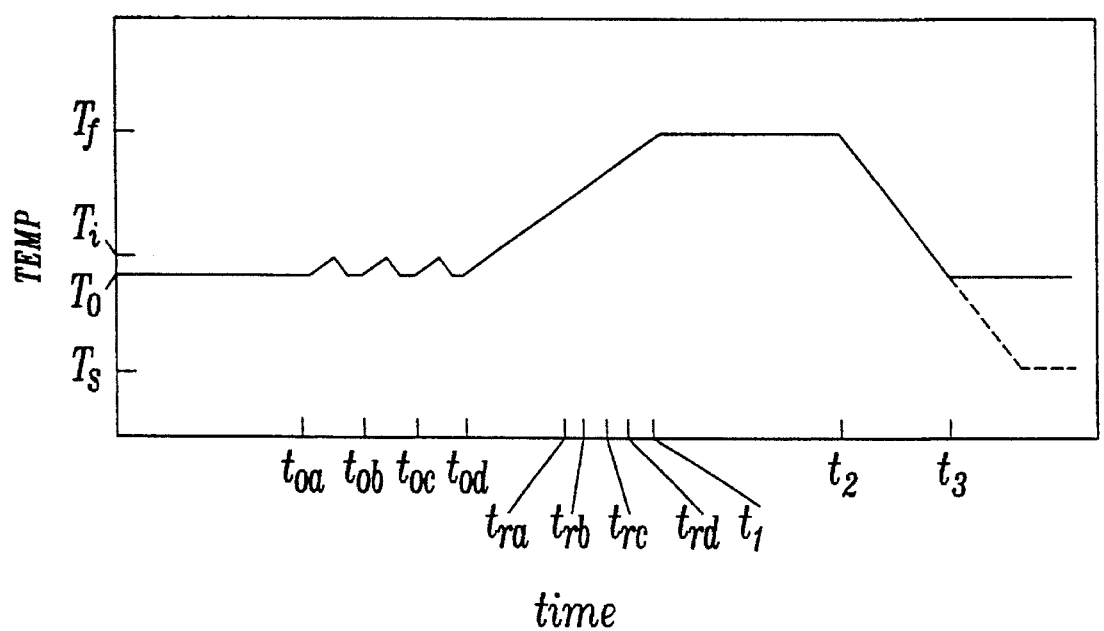
FIG. 3 provides a chart of a preferred embodiment of a time/temperature operating sequence for concurrent gas chromatographic analysis of four analyte specimens in accordance with the present invention.

The method of the present invention involves sequential loading of multiple analyte specimens in discrete bands within an analytical column prior to elution of the specimens through the column. A time/temperature sequence suitable for operation of a gas chromatograph in accordance with the present invention is shown in FIG. 3. The gas chromatograph is initially maintained at a temperature $T_0$. At a time $t_{0a}$, the first analyte specimen is introduced to the inlet of the column. The column is then heated to an intermediate temperature designated as $T_i$, which is slightly above the initial temperature $T_0$. The temperature $T_i$ is selected to allow the analyte specimen to just enter the column a short distance.

Once this intermediate temperature $T_i$ is reached, the column temperature is allowed to immediately return back to the initial temperature $T_0$, by opening the column chamber in the gas chromatograph to vent heat. As soon as the column has returned to the initial temperature $T_0$, a second analyte specimen is introduced at time $t_{0b}$. The column is then again heated at a constant rate to the intermediate temperature $T_i$, followed by immediate return to the initial temperature $T_0$ for introduction of a third specimen at time $t_{0c}$. As soon as the third specimen has been introduced, the temperature of the column is again raised slightly at a constant rate to the intermediate temperature $T_i$, followed by immediate return again to the initial temperature $T_0$. At that time designated as $t_{0d}$, a fourth specimen is then added.

In the example shown in FIG. 3, only four specimens are added, and the temperature of the column is then raised at a constant rate and the analytes are eluted at times $t_{ra}$, $t_{rb}$, $t_{rc}$ and $t_{rd}$. This final temperature, $T_f$, is reached at a time $t_1$. The temperature $T_f$ is then maintained constant until time $t_2$, which is predetermined to be sufficient to enable all extraneous analytes to elute from the column. At this point, the column is allowed to return back to the initial temperature $T_0$ for introduction of additional multiple analyte specimens, or alternately, to a stand-by temperature of $T_s$.

Preferably the intermediate temperature $T_i$ is closer to the initial temperature $T_0$ than to the final temperature $T_f$. The temperature is selected to enable rapid loading of the multiple sample specimens in order to minimize the total time duration required for analysis of all samples, while still ensuring that the specimens are spaced within the column. During the elution time prior to $t_1$, analytes from each specimen, indicated as specimens a, b, c, and d, elute in discrete bands. For example, for the analysis of MMA, the MMA ester from specimen a will elute from the column outlet first, followed in short duration thereafter by the MMA ester from specimen b, followed by the MMA ester from specimen c, followed by the MMA ester from specimen d. The MMA ester from each specimen elutes as a discrete band, so that specimen integrity is maintained.

While FIG. 3 has been illustrated for loading of four analyte specimens, it should be readily apparent that a lesser number of at least two analyte specimens, or a greater number, could be employed. Additionally, in FIG. 3 the rate of temperature increase from the initial temperature $T_0$ to the intermediate $T_i$ is illustrated as being the same as the rate of increase from the initial temperature $T_0$ to the final temperature of $T_f$. These rates may be varied as desired, provided that subsequent specimens are loaded sequentially in spaced relationship within the column.

Figure 4:
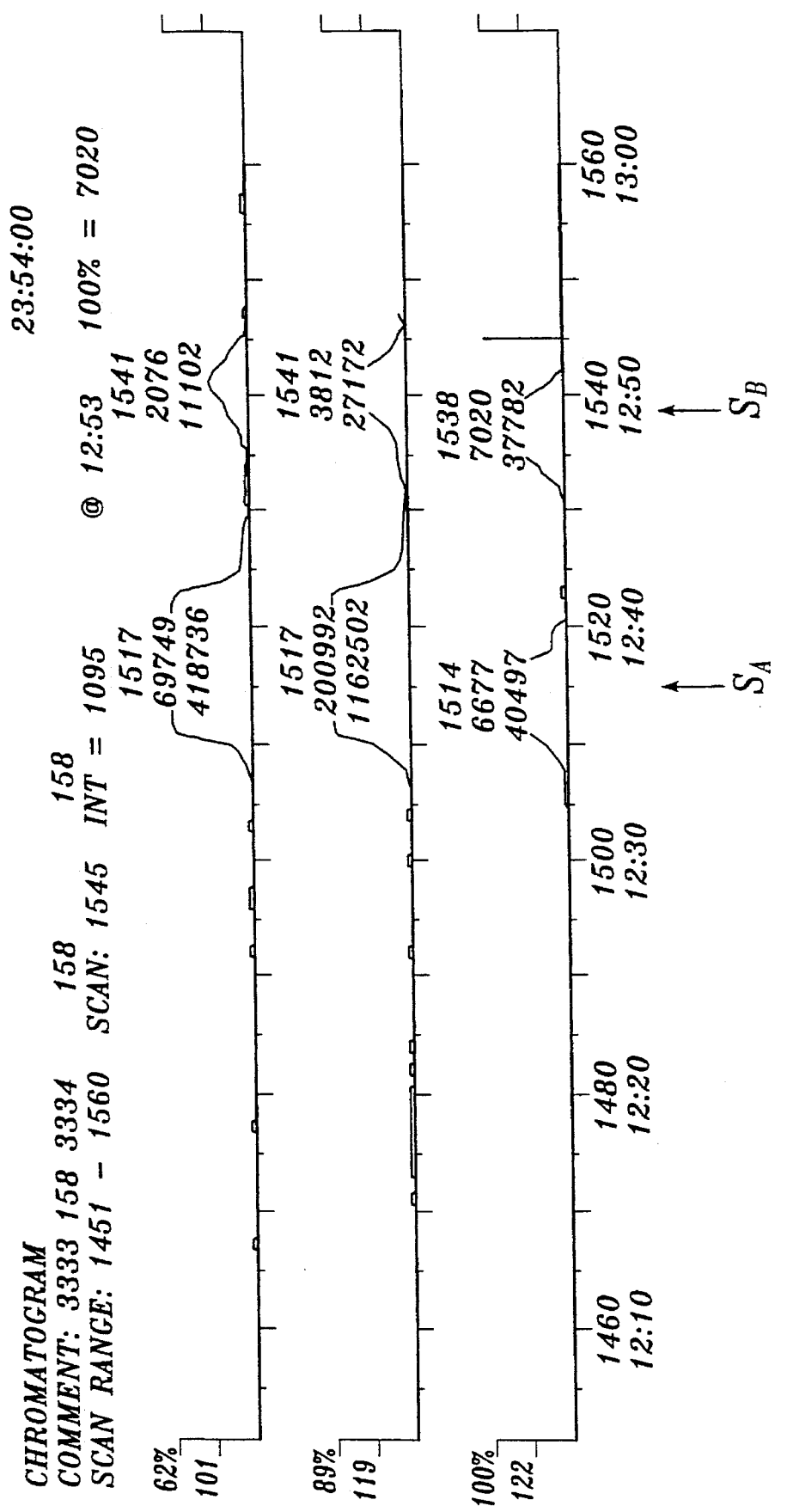
FIG. 4 provides a mass spectrometer chromatogram produced by concurrent analysis of the MMA content of two urine specimens in accordance with the present invention.
Figure 5:
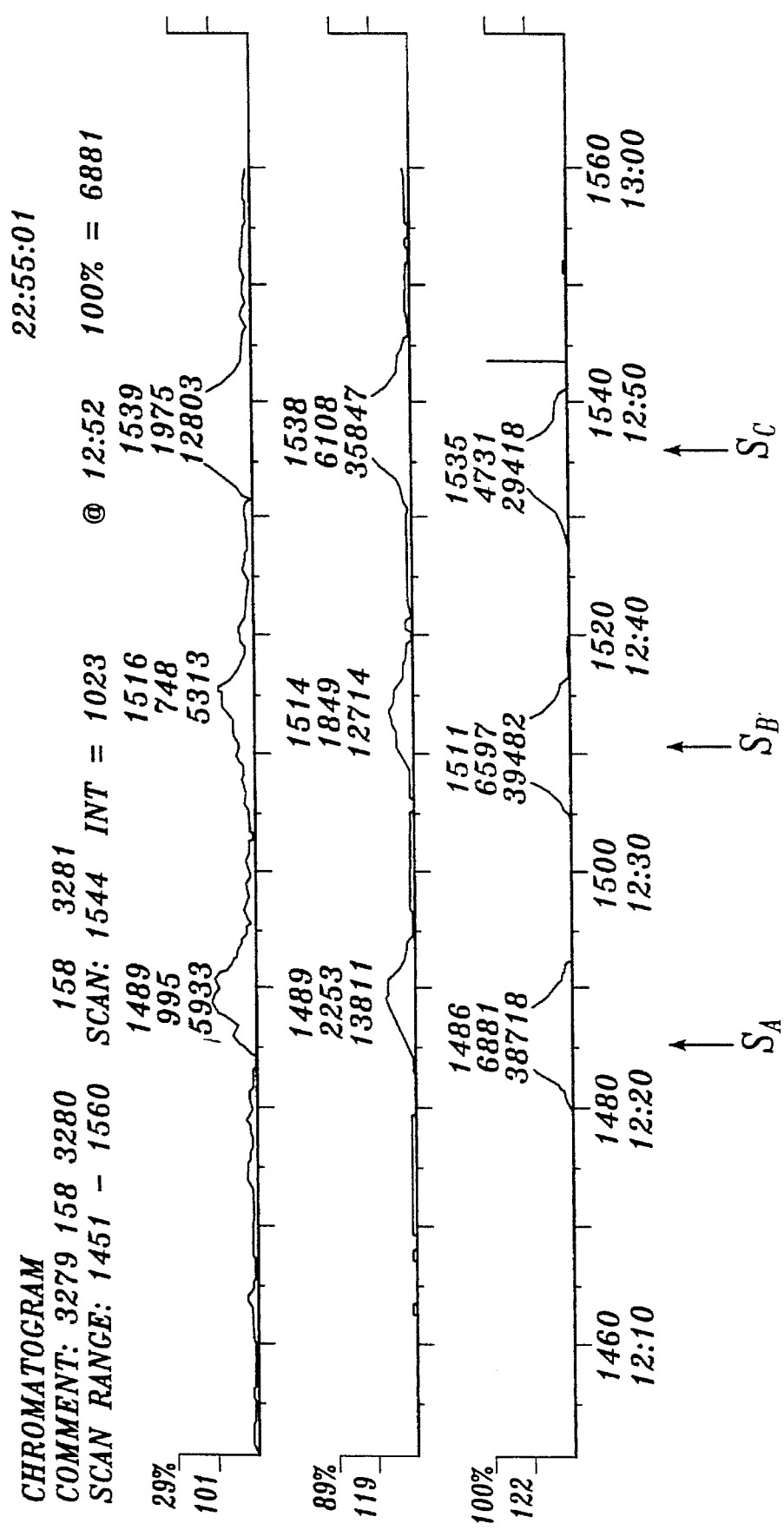
FIG. 5 provides a mass spectrometer chromatogram produced by concurrent analysis of the MMA content of three urine specimens in accordance with the present invention.
Figure 6:
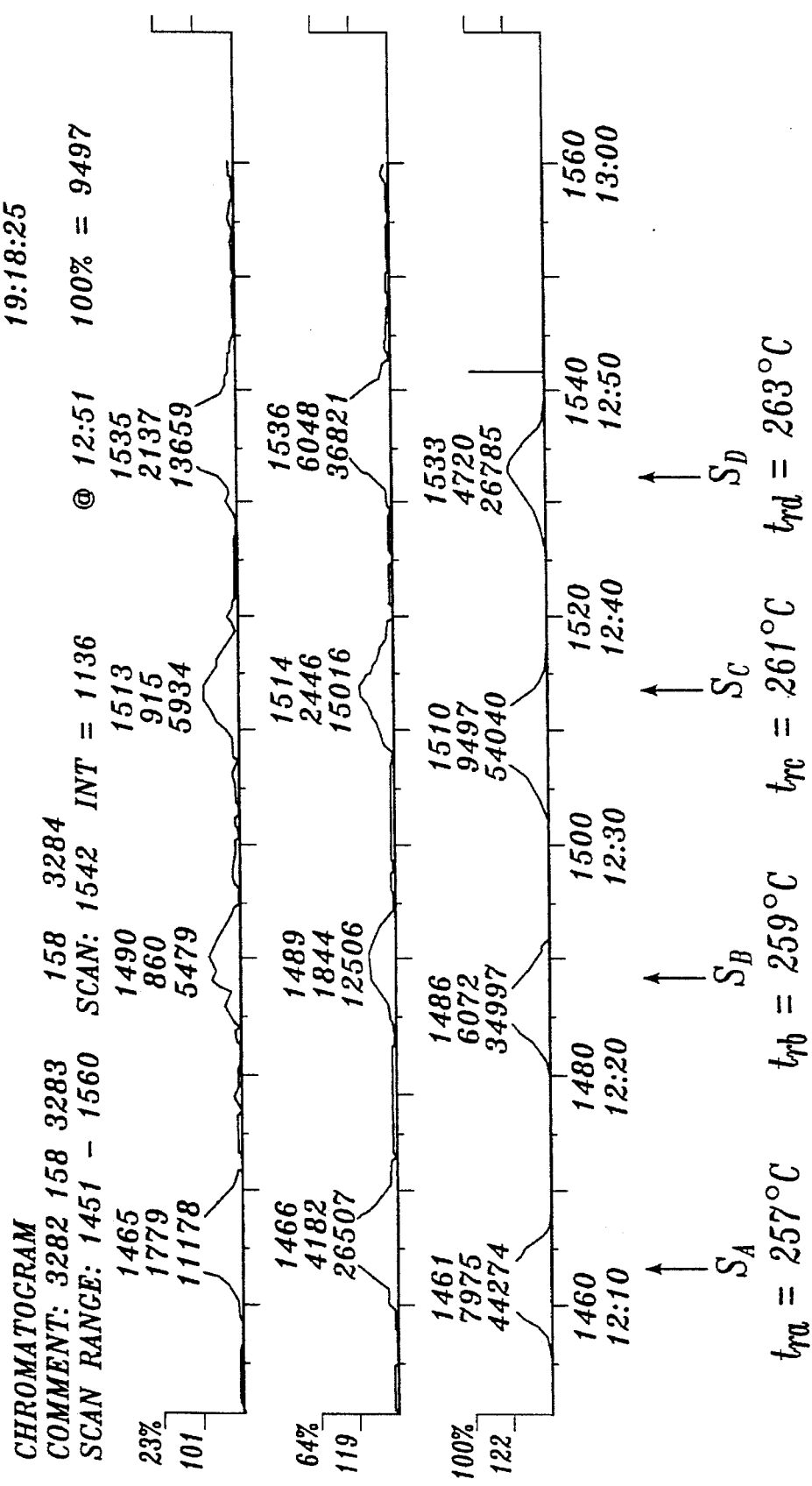
FIG. 6 provides a mass spectrometer chromatogram produced by concurrent analysis of the MMA content of four urine specimens in accordance with the present invention following the time/temperature schedule of FIG. 3.

To illustrate a preferred embodiment of the present invention, FIGS. 4–6 provide mass spectrometry chromatograms produced using the method of the present invention to analyze multiple urine specimens for MMA content. In each case, the urine specimens were first prepared using creatinine determination, addition of a deuterated standard, and dicyclohexyl esterification, in accordance with the conventional method previously described. This conventional preparation of samples is to be distinguished from the subsequent method in which they are loaded into the gas chromatograph column, which is not in accordance with conventional techniques.

Referring to FIG. 4, this chromatogram was obtained as follows: The gas chromatograph was maintained at an initial temperature of 140° C. A first specimen, indicated in FIG. 4 as $S_A$, was injected, followed by immediate increase in temperature at a rate of 10° C. per minute to an intermediate temperature of 158° C. The column temperature was then immediately allowed to return to the initial temperature of 140° C., at a rapid rate as determined by the ability of the gas chromatograph to vent heat. The second specimen, indicated as specimen $S_B$, was then immediately injected at the initial temperature of 140° C. The column temperature was then increased at a rate of 10° C. per minute to the final temperature of 270° C., which was maintained for ten minutes. This caused two discrete bands of MMA esters, corresponding to specimens $S_A$ and $S_B$, to travel concurrently through and elute sequentially from the gas chromatograph column and into the mass spectrometer in discrete bands at 261° C. and 263° C., respectively. These discrete bands are indicated in FIG. 4, with peaks in strips 101 and 119 again corresponding to the MMA esters, while the peaks in strips 122 correspond to the deuterated MMA ester standard.

FIGS. 5 and 6 provide further examples in which three and four, respectively, urine specimens were loaded onto the gas chromatograph and then concurrently analyzed. The same method as that used to generate the chromatogram of FIG. 4 was utilized. However, in the chromatogram of FIG. 5, after the introduction of the second specimen $S_B$, the chromatograph temperature was increased only to the intermediate temperature of 158° C., followed by immediate return to the initial temperature of 140° C. and immediate injection of the third specimen $S_C$. The column temperature was then increased to the final temperature of 270° C., and held for ten minutes to allow all three MMA ester specimens to sequentially elute from the column and into the mass spectrometer.

The chromatogram of FIG. 6 was derived in the same fashion as FIG. 5, except that after addition of the third specimen $S_C$, a fourth specimen $S_D$ was loaded in the same manner, resulting in the elution of four separate MMA ester bands at 257° C., 259° C., 261° C. and 263° C., respectively.

The temperatures and rate of temperature increase and durations given above are provided by way of example only. Other temperatures and rates of heating may be readily determined by those of ordinary skill in the art for use with particular length and types of columns. Further, the intermediate temperature and the rate of heating thereto may be controlled to determine the spacing between multiple samples within the column, as desired to ensure sample integrity. For example, for the urinalysis example provided, when using an initial temperature of 140° C. and a final temperature of 270° C., an intermediate temperature of less than 200° C. may be selected with an intermediate temperature of 158° C. being found to be preferred.

While the above method has been described as suitable for methylmalonic acid urinalysis, the same method of concurrent multiple sample analysis may be utilized for the analysis of any other chemical component of urine or any other compositions. Further, rather than using a gas chromatograph coupled with a mass spectrometer, it is possible to use a gas chromatograph alone in situations where the particular components within a composition are well characterized. Finally, the method of the present invention may also be utilized for other types of chromatography, such as a high pressure liquid chromatography coupled with other detection instruments as previously stated.

Figure 7:
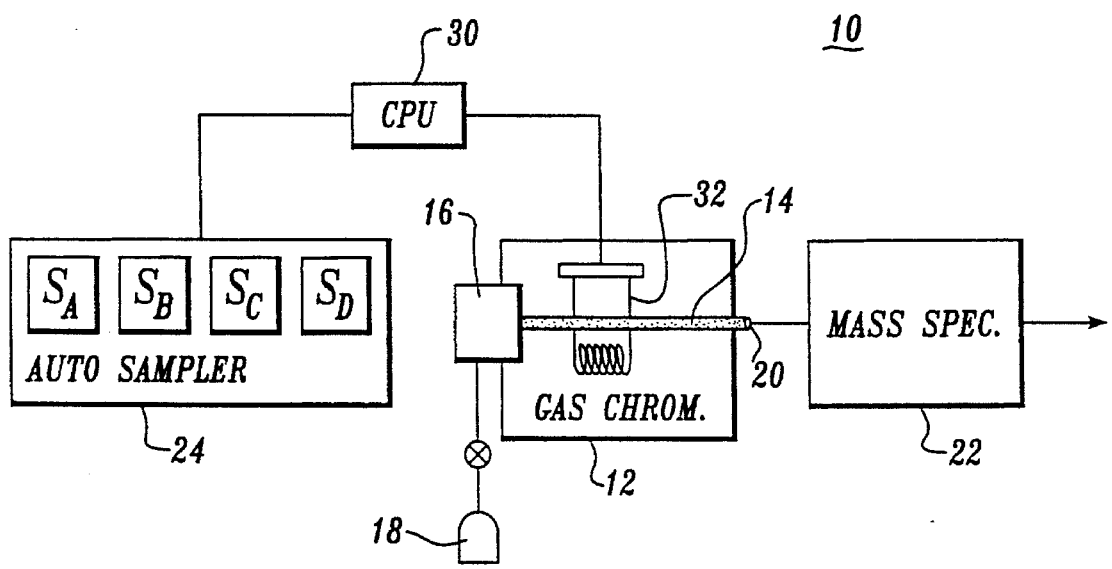
FIG. 7 provides a schematic diagram of a gas chromatography/mass spectrometry system including capacity for automatic introduction of multiple specimens for concurrent analysis in accordance with the present invention.

The chromatograms of FIGS. 4–6 were generated using manual injection of the multiple specimens. The present invention also entails an automated system for introduction of the multiple specimens to the analyte column. One such system 10 in accordance with the present invention is shown in FIG. 7. System 10 includes a gas chromatograph 12 containing an analytical column 14. The injection chamber 16 of the gas chromatograph column is supplied with a carrier fluid, such as an inert gas, from a carrier fluid reservoir 18. The outlet 20 of the column 14 is coupled to a mass spectrometer 22.

The system includes an autosampler 24 that is connected between the carrier fluid reservoir 18 and the injection chamber 16 of the column 14. One suitable autosampler is a model CTC-A200 autosampler, available from Finnigan MAT Corporation, San Jose, Calif. This autosampler, for example, has a 200 sample vial capacity and can be programmed to draw up a few microliters from a selected sample vial with a syringe, traverse the syringe to the injector of a gas chromatograph, inject the sample through a septum into the injection chamber 16 (maintained at about 250° C.), and then rinse the syringe. The autosampler may be programmed in accordance with the present invention to sequentially sample and inject samples from a selected one of multiple sample reservoirs, designated in FIG. 7 as reservoirs $S_A$, $S_B$, $S_C$, and $S_D$.

The operation of the autosampler 24 is controlled by a central processing unit 30. The central processing unit 30 can be housed within a stand-alone personal computer or can be included as a dedicated processor integrated with the gas chromatogram 12 and the autosampler 24. The central processing unit 30 also controls operation of a heating element 32 that heats a chamber in which is housed gas chromatograph column 14. The central processing unit 30 is programmed through a user interface, such as a keyboard (not shown), to operate the autosampler 24 and the gas chromatogram 12 in accordance with the present invention.

In particular, the central processing unit 30 first controls the autosampler 24 to inject a sample from the first sample reservoir $S_A$ into the injection chamber 16 of the gas chromatograph column 14, followed by control of the heater 32 to raise the temperature of the gas chromatograph column 14 from an initial temperature to an intermediate temperature. The operation of the heater 32 is then stopped by the central processing unit 30, and the chromatograph column 14 is cooled, also as controlled by the central processing unit 30. When the initial temperature has again been reached, an additional sample is loaded, in accordance with the method previously described. This is continued until all samples have been loaded, followed by heating to the final temperature.

While the preferred embodiment of the invention has been illustrated and described, it will be appreciated that various changes can be made therein without departing from the spirit and scope of the invention. It is therefore intended that the scope of letters patent granted hereon be limited only by the definitions contained in the appended claims.

The embodiments of the invention in which an exclusive property or privilege is claimed are defined as follows:

1. A method for chromatographic separation of multiple analyte specimens using an analytical column containing a selective adsorbent media through which column a carrier fluid flows, the method comprising:

introducing a first analyte specimen into the analytical column at an initial temperature;

heating the analytical column to an intermediate temperature to cause the first analyte specimen to partially travel into the column;

cooling the analytical column to the initial temperature;

introducing a second analyte specimen into the analytical column; and heating the analytical column to a final temperature greater than the intermediate temperature, causing analyte from the first analyte specimen and analyte from the second analyte specimen to concurrently and discretely travel through, and sequentially elute from, the analytical column.

2. The method of claim 1, further comprising, after the introduction of a second analyte specimen:

heating the analytical column to the intermediate temperature to cause the second analyte specimen to partially travel into the column a distance discretely spaced from the first analyte specimen;

cooling the analytical column to the initial temperature;

introducing a third analyte specimen into the analytical column; and heating the analytical column to the final temperature, causing analyte from the first, second, and third analyte specimens to concurrently and discretely travel through, and sequentially elute from, the analytical column.

3. The method of claim 2, further comprising, after the introduction of the third analyte specimen:

heating the analytical Column to the intermediate temperature to cause the third analyte specimen to partially travel into the column a distance discretely spaced from the second analyte specimen;

cooling the analytical column to the initial temperature;

introducing at least a fourth analyte specimen into the analytical column; and heating the analytical column to the final temperature, causing analyte from the first, second, third and fourth analyte specimens to concurrently and discretely travel through, and sequentially elute from, the analytical column.

4. The method of claim 1, wherein the analytical column comprises a gas chromatography column.

5. The method of claim 4, further comprising analysis of sequentially eluted analyte from the first and second analyte specimens using a mass spectrometer as the analytes elute from the gas chromatography column.

6. The method of claim 1, wherein the first and second analyte specimens comprise urine specimens.

7. The method of claim 6, wherein the analytical column comprises a gas chromatography column.

8. The method of claim 7, further comprising receiving the sequentially eluted analyte from the first and second analyte specimens for qualitative or quantitative analysis.

9. A method for chromatographic separation of multiple analyte specimens using an analytical column containing a selective adsorbent media, through which column a carrier fluid flows, the method comprising:

introducing a first analyte specimen into the analytical column at a first temperature;

heating the analytical column to a second temperature to cause the first analyte specimen to partially travel into the column;

cooling the analytical column to the first temperature;

introducing a second analyte specimen into the analytical column; and heating the analytical column to a third temperature to cause analyte from the first analyte specimen and analyte from the second analyte specimen to concurrently and discretely travel through, and sequentially elute from, the analytical column.

10. A method of chromatographic separation prior to urinalysis to determine the concentration of methylmalonic acid in multiple urine specimens using gas chromatography, the method comprising:

introducing a first urine specimen into a gas chromatograph column at an initial temperature;

heating the gas chromatograph column to an intermediate temperature to cause methylmalonic acid from the first urine specimen to partially travel into the gas chromatograph column;

cooling the gas chromatograph column to the initial temperature;

introducing a second urine specimen into the gas chromatograph column; and heating the gas chromatograph column to a final temperature greater than the intermediate temperature, causing methylmalonic acid bands from the first and second urine specimens to concurrently and discretely travel through, and sequentially elute from, the gas chromatograph column.

11. The method of claim 10, further comprising analysis of sequentially eluted analyte from the first and second analyte specimens using a mass spectrometer as the analytes elute from the gas chromatograph column.

12. The method of claim 10, wherein the initial temperature comprises 140° C., the final temperature comprises 270° C., and the intermediate temperature comprises a temperature of less than 200° C.

13. The method of claim 10, further comprising, after the introduction of a second urine specimen:

heating the gas chromatograph column to the intermediate temperature to cause the second urine specimen to partially travel into the column a distance discretely spaced from the first urine specimen;

cooling the gas chromatograph column to the initial temperature;

introducing a third urine specimen into the gas chromatograph column; and heating the gas chromatograph column to the final temperature, causing methylmalonic acid bands from the first, second, and third urine specimens to concurrently and discretely travel through, and sequentially elute from, the gas chromatograph column.

14. The method of claim 13, further comprising, after the introduction of the third urine specimen:

heating the gas chromatographic column to the intermediate temperature to cause the third urine specimen to partially travel into the column a distance discretely spaced from the second urine specimen;

cooling the gas chromatographic column to the initial temperature;

introducing at least a fourth urine specimen into the gas chromatograph column; and heating the gas chromatographic column to the final temperature, causing methylmalonic acid bands from the first, second, third and fourth urine specimens to concurrently and discretely travel through and sequentially elute from, the gas chromatograph column.

15. An instrument for use in analysis of multiple analyte specimens contained in specimen reservoirs that are selectively sampled by operation of a specimen introduction means for introducing sampled specimens into a carrier fluid stream, the instrument comprising:

a source of supply of a carrier fluid stream;

a column containing selective adsorbent media and having an inlet and outlet, the carrier fluid stream flowing into the column inlet from the source of supply of the carrier fluid stream;

specimen introduction means for selectively introducing samples of analyte specimens from specimen reservoirs into the carrier fluid stream at the column inlet;

a heater for selective application of heat to the column; and control means for controlling the heater and the specimen introduction means for: automatically and sequentially introducing a first analyte specimen into the inlet of the column at an initial temperature; heating the column to an intermediate temperature to cause the first analyte specimen to partially travel into the column; allowing the column to cool to the initial temperature; introducing a second analyte specimen into the column; and heating the column to a final temperature greater than the intermediate temperature to cause analyte from the first analyte specimen and analyte from the second analyte specimen to concurrently and discretely travel through, and sequentially elute from, the outlet of the column.

* * * * *

UNITED STATES PATENT AND TRADEMARK OFFICE
CERTIFICATE OF CORRECTION

PATENT NO. : 5,508,204
DATED : April 16, 1996
INVENTOR(S) : E.J. Norman

It is certified that error appears in the above-indentified patent and that said Letters Patent is hereby corrected as shown below:

| COLUMN | LINE | |
|---|---|---|
| 10 (Claim 14, | 3 line 1) | "alter" should read --after-- |

Signed and Sealed this

Twenty-seventh Day of August, 1996

Attest:

BRUCE LEHMAN

*Attesting Officer*     *Commissioner of Patents and Trademarks*